(12) United States Patent
Howah

(10) Patent No.: US 9,001,228 B2
(45) Date of Patent: Apr. 7, 2015

(54) IMAGE SENSOR SYSTEM FOR DETECTING IMAGE INFORMATION FOR AUTOMATIC IMAGE DATA PROCESSING

(75) Inventor: Lothar Howah, Gladbeck (DE)

(73) Assignee: Westfaelische Hochschule Gelsenkirchen, Bocholt, Recklinghausen, Gelsenkirchen (DE)

( * ) Notice: Subject to any disclaimer, the term of this patent is extended or adjusted under 35 U.S.C. 154(b) by 61 days.

(21) Appl. No.: 13/502,741

(22) PCT Filed: Oct. 20, 2010

(86) PCT No.: PCT/EP2010/006404
§ 371 (c)(1),
(2), (4) Date: Apr. 19, 2012

(87) PCT Pub. No.: WO2011/047847
PCT Pub. Date: Apr. 28, 2011

(65) Prior Publication Data
US 2012/0206616 A1    Aug. 16, 2012

(30) Foreign Application Priority Data
Oct. 20, 2009  (DE) .......................... 10 2009 050 073

(51) Int. Cl.
*H04N 5/225* (2006.01)
*H04N 5/335* (2011.01)
(Continued)

(52) U.S. Cl.
CPC ........... *H04N 5/335* (2013.01); *G01N 21/8806* (2013.01); *G01N 21/8851* (2013.01); *H04N 5/247* (2013.01)

(58) Field of Classification Search
CPC .............. H04N 5/2258; H04N 5/3415; H04N 5/23238; H04N 5/2624
USPC ........................ 348/218.1, 207.99, 373, 375
See application file for complete search history.

(56) References Cited

U.S. PATENT DOCUMENTS 4,908,751 A    3/1990   Smith
5,464,984 A   11/1995   Cox et al.
(Continued)

FOREIGN PATENT DOCUMENTS

DE    699 01 030 T2    7/2002
EP     1 223 739 A1    7/2002
WO   WO 2007/014293 A1  2/2007

OTHER PUBLICATIONS

B. Wilburn et al.: "High Performance Imaging Using Large Camera Arrays", ACM Transactions on Graphics, vol. 24, No. 3, pp. 765-776 (Jul. 1, 2005).

(Continued)

*Primary Examiner* — Antoinette Spinks
(74) *Attorney, Agent, or Firm* — Norman B. Thot

(57) ABSTRACT

An image sensor array for capturing image information for automatic image data processing. The image sensor array includes a multiplicity of identical sensor cells. Each sensor cell respectively comprises at least one image sensor with a dedicated sensor optical system. A frame buffer is configured to store image information from the at least one image sensor. An evaluation unit is configured to process the image information. At least one data interface to a directly adjacent sensor cell. The sensor cells are arranged in at least one row so that a capture region of an image sensor of the directly adjacent sensor cell overlaps. The at least one data interface to the directly adjacent sensor cell is configured to access the image data of the capture region. The respective valuation unit of the sensor cells is configured to determine a correlation of items of the image data in the capture region.

23 Claims, 9 Drawing Sheets

(51) Int. Cl.
  *G01N 21/88* (2006.01)
  *H04N 5/247* (2006.01)

(56) References Cited

U.S. PATENT DOCUMENTS

| | | |
|---|---|---|
| 6,005,911 A | 12/1999 | Cheung |
| 6,920,180 B1 | 7/2005 | Yamane et al. |
| 7,215,364 B2 | 5/2007 | Wachtel et al. |
| 7,715,928 B1 * | 5/2010 | Ciancio et al. ................. 700/1 |
| 2004/0196378 A1 * | 10/2004 | Kannermark et al. ... 348/207.99 |
| 2004/0201669 A1 | 10/2004 | Guha et al. |
| 2006/0215038 A1 | 9/2006 | Gruber et al. |
| 2009/0268983 A1 | 10/2009 | Stone et al. |
| 2012/0206616 A1 * | 8/2012 | Howah ....................... 348/218.1 |

OTHER PUBLICATIONS

M. Levoy: "Light Fields and Computational Imaging", Computer, IEEE Service Center, vol. 39, No. 8, pp. 46-55 (Aug. 2006).

L. Howah: "Line Scan Cameras in Multiple Sensor Systems", Aise Steel Technology, vol. 78, No. 2, pp. 48-51 (Feb. 2001).

C. S. Iiong et al.: "Single-Chip Camera Modules for Mosaic Image Sensor", Proc. SPIE, vol. 4306, pp. 227-238 (2001).

Hunt Engineering, HETVIO2-'C44-Based Video I/O Module User Manual, Document Rev E, M. Siggins Jun. 7, 1999, pp. 1-34 (1999).

\* cited by examiner

IMAGE SENSOR SYSTEM FOR DETECTING IMAGE INFORMATION FOR AUTOMATIC IMAGE DATA PROCESSING

CROSS REFERENCE TO PRIOR APPLICATIONS

This application is a U.S. National Phase application under 35 U.S.C. §371 of International Application No. PCT/EP2010/006404, filed on Oct. 20, 2010 and which claims benefit to German Patent Application No. 10 2009 050 073.1, filed on Oct. 20, 2009. The International Application was published in German on Apr. 28, 2011 as WO 2011/047847 A1 under PCT Article 21(2).

FIELD

The present invention provides an image sensor array for capturing image information for automatic image data processing, having a multiplicity of identical sensor cells, which respectively have an image sensor with a dedicated sensor optical system, a frame buffer for storing image information from the image sensor, and an evaluation unit for processing the image information, the sensor cells being arranged in at least one row such that the capture regions of the image sensors of directly adjacent sensor cells overlap.

BACKGROUND

In many technical problems for controlling industrial plants, or for the quality control thereof, the basic object consists of inspecting the surface of an object, establishing a dimensional variable and comparing this to a reference variable. Primary measurement variables such as position, length, width or height serve for establishing secondary variables such as area, volume, dimensional accuracy, completeness or the like.

Solving these metrological objects in a quick and contactless fashion, i.e. without wear-and-tear, is a feature of special technology, which records images from the scene of a measurement object and evaluates said images using methods and algorithms from so-called image data processing. These technologies are subsumed under the heading industrial image processing (IIP) and have a broad spectrum of technical applications. Thus, for example, image data processing also has applications in medicine, agriculture or security technology.

Optimizing industrial production methods is a specific challenge from the totality of all applications and, as a result, offers the reduction of rejects or the primarily utilized raw products, and also the reduction in secondary factors such as energy use and ecological harm. By using IIP, an increase in quality and productivity of production plants is pursued, which is reflected in an increase in the efficiency, international competitiveness and securing of jobs.

In order to secure product quality and plant availability, producers of tape- or web materials use inspection systems that typically consist of a multiplicity of cameras, with one respective image sensor. Solutions for maximizing the information obtained from image scenes using methods of multi-sensorial data fusion are also sought after in numerous research establishments active in the research field of technical image processing. Here, the data from a plurality of sensors is combined. Compared to processing individual image scenes, the fused image information allow further conclusions to be drawn in respect of physical events, activities or situations.

The limitations to the use of industrial image processing become apparent in the field of belt inspection systems. Particularly in the case of small production plants with few high-quality goods, the high investment requirements of an IIP system do not always make economic sense because the components used therein are very cost intensive. In addition to this, there is small installation space in small production machines or lack of qualified staff, which prevents the integration of the systems.

Industrial image-processing systems have a signal chain that essentially consists of illumination, imaging optical system, image recorder, data interface and evaluation computer in a single or multiple arrangement. The systems differ according to their type and number in the light sources, the objectives, the sensor technology, the data interface and the evaluation computer. By combining these components in conjunction with appropriate algorithms, it is possible to solve many problems. However, if the measurement should be conducted on a large measurement field, for example, a few hundred centimeters, and, at the same time, at a small distance from the measurement plane or object plane, then complex and comparatively expensive IIP systems are required. Until now, there has been no IIP system, not even as a result of any combination and number of the components listed above, commercially available that constitutes an economically justifiable solution for recording and evaluating large image scenes without distortion or parallax in the case of small installation space, high scene resolution and, at the same time, a high image repetition rate (i.e., measurement rate). However, these features are required simultaneously within many technical applications.

FIG. 1 shows a typical arrangement of an elementary IIP system. Here, a camera 100 is connected to a PC 140. The camera 100 has a field of view 110, also referred to as capture region below, within which an object to be inspected 120, more particularly a component, is arranged, the surface of which forming the object plane 130 to be recorded. The camera records an image scene in which the component 120 is inspected in respect of completeness and/or dimensional accuracy. To this end, the field of view 110, which completely captures the object to be inspected 120, is set in the object plane 130 by selecting a suitable optical imaging system, i.e., of the camera objective. If the measurement object occurs within a machine, the relatively large distance of the camera 100 from the object plane 130 has an effect as a technical barrier.

In order to reduce the object distance, it would be possible to select an objective with a smaller focal length; however, this would have a disadvantageous effect on the imaging performance of the objective. However, the dependence of the imaging factor $\beta'$ on the object distance, which is now stronger, is of greater importance here for metrological objects. One possible solution lies in the use of objectives with an object-side telecentric beam path. In order to avoid perspective errors, use can be made of telecentric optical systems (TCOs). These are virtually free of perspectives within the telecentric range. By means of a TCO, objects, irrespective of the object plane thereof, are always recorded in the same reproduction scale. However, the image field of a TC optical system is naturally always smaller than the diameter of the exit lens of the objective and hence it is restricted to a few centimeters. A TC objective with a diameter of 15 cm, however, requires extensive installation space and intensive light sources, and is expensive. IIP systems operating on telecentric principles are hence currently used to measure small parts.

An alternative to this lies in subdividing the measurement region to a plurality of cameras; however, this quickly reaches the limitations of modern frame grabbers and also PCs in the case of a large number of cameras, and moreover creates significant costs. Here, a plurality of conventional cameras are arranged in rows or in the form of a matrix, and are connected to a PC via a conventional frame grabber. However, if this technology were wanted to be used, for example, to construct a matrix of 32×32 cameras, the problem would arise that the 1024 signal lines would not be contacted to any conventional evaluation computer or PC. Conventional PCs are able to incorporate up to four PCI expansion cards or frame grabbers. Even if each frame grabber in turn had four signal channels, it would only be possible to connect 16 cameras to each PC. The restricted computational power of modern PCs and the fact that 64 PCs would be required illustrates this unsuitable system arrangement here. In addition to the high costs overall for the cameras and frame grabbers, the costs of PC plug-in modules and 19" cabinets for the housing, and the installation space for the switchgear cabinet, the difficult maintainability constitutes a further defect in respect of an integration into industrial surroundings.

In applications where there are high demands on the scene resolution and only little installation space is available, the camera or image sensor is often these days displaced in a translational manner to the relevant image region (region of interest, ROI) by means of a motor-driven xy-drive. This makes it possible to obtain very high resolutions of the scene with high imaging performance. By using appropriate path measurement systems (glass scales) of the translational drives, it is also possible to achieve low measurement uncertainty. Nevertheless, this system constellation also has significant disadvantages. Recording or scanning the scene requires a lot of time since the positioning of the image sensor requires a few 100 ms. Moreover, a mechanical drive is not maintenance-free and free from wear-and-tear, and hence it has a relatively short service life.

SUMMARY

An aspect of the present invention is to provide a maintenance-free and reliable image capture unit and a method for an image-processing system, which, with a small distance to the measurement plane, is able to record without distortion or parallax a large image scene with a high scene resolution and, at the same time, a high bit repetition rate, and also leads to low costs in production and application.

In an embodiment, the present invention provides an image sensor array for capturing image information for automatic image data processing. The image sensor array includes a multiplicity of identical sensor cells. Each sensor cell respectively comprises at least one image sensor with a dedicated sensor optical system. A frame buffer is configured to store image information from the at least one image sensor. An evaluation unit is configured to process the image information. At least one data interface to a directly adjacent sensor cell. The sensor cells are arranged in at least one row so that a capture region of an image sensor of the directly adjacent sensor cell overlaps. The at least one data interface to the directly adjacent sensor cell is configured to access the image data of the capture region. The respective evaluation unit of the sensor cells is configured to determine a correlation of items of the image data in the capture region.

BRIEF DESCRIPTION OF THE DRAWINGS

The present invention is described in greater detail below on the basis of embodiments and of the drawings in which.

DETAILED DESCRIPTION

Figure 1:
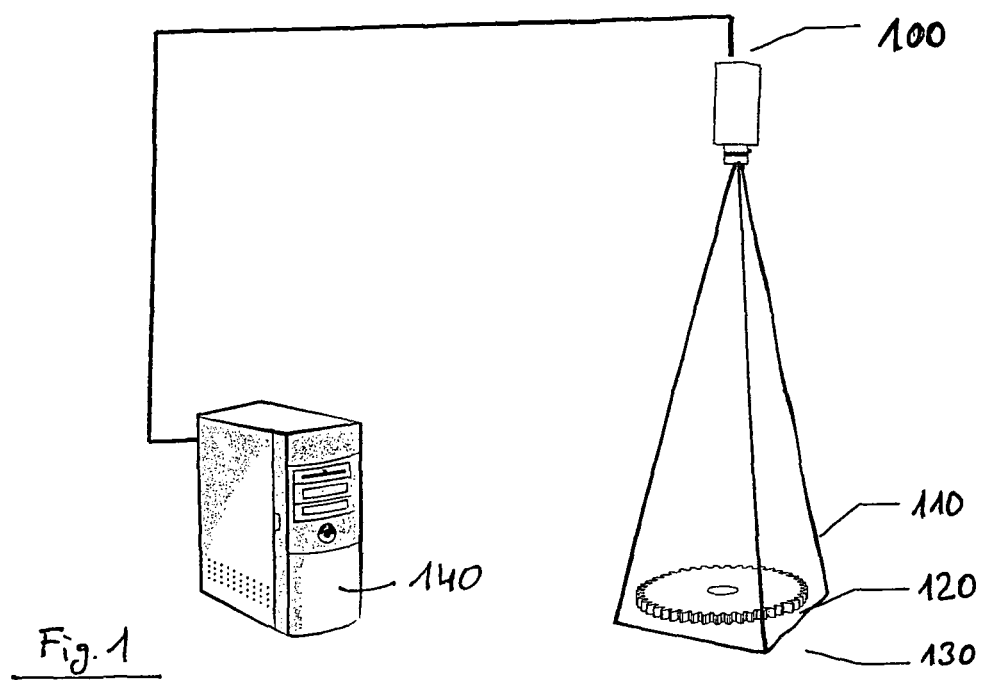
FIG. 1 shows a conventional image-processing system for measuring an object.

In an embodiment of the present invention, an image sensor array for capturing image information for automatic image data processing is proposed having a multiplicity of identical sensor cells which respectively have an image sensor with a dedicated sensor optical system, a frame buffer for storing image information from the image sensor, and an evaluation unit for processing the image information, the sensor cells being arranged in at least one row such that the capture regions of the image sensors of directly adjacent sensor cells overlap, wherein each sensor cell has at least one data interface to an adjacent sensor cell, by means of which the image data of the overlapping capture region of the adjacent sensor cell can be accessed, with the evaluation units respectively being configured to determine a correlation of these items of image data.

In an embodiment of the method according to the present invention for capturing image information for automatic image data processing by means of the above-described image sensor array, each image sensor of a sensor cell captures a sub-region of an object plane and stores the image data in the frame buffer of the sensor cell, with the capture regions of the image sensors from directly adjacent sensor cells overlapping. The image data of the overlapping capture region from the adjacent sensor cells is furthermore accessed via the data interfaces. The evaluation units of the sensor cells respectively determine a correlation of these items of image data.

The sensor array according to the present invention leads to novel solutions of technical measurement and inspection objects using methods from industrial image processing. Conventional cameras mainly have point-to-point data interfaces. Owing to a low data rate of these networks, the few commercially available cameras that are equipped with network interfaces do not offer sufficiently fast communication options between the image sensors and the image-processing processor (frame grabber/evaluation computer) in order to evaluate proximity relationships, as the sensor array according to the present invention is able to carry out. Conventional IIP systems virtually have a physical star topology and hence a corresponding bottle neck to the evaluation processor.

As a result of the fact that each sensor cell has a dedicated evaluation unit, this distributes the computational power toward the image sensor. In the image sensor array according to the present invention, this leads to a scalable increase in the computational power and a scalable resolution of the image scene. This moreover moves the computationally intensive data pre-processing to the point of the data generation. The image sensor array operates at a high measurement rate because image data was already evaluated, and extracted scene information was generated, in the sensor array for each image sensor.

The number of sensor cells can be selected arbitrarily; in particular, it can be matched to the size of the image scene to be captured. Here, within the meaning of the present invention, a multiplicity of sensor elements is understood to mean at least a number in the upper single-digit region, up to a number of tens or even one hundred sensor cells. The image sensors have high connectivity via their data interfaces. As a result of each image sensor having a dedicated sensor optical system, these form autonomous optical imaging systems which are otherwise only known from the animal kingdom.

By arranging the sensor cells and selecting the sensor optical systems such that the capture regions of the image sensors of adjacent sensor cells overlap, it is possible to achieve a small object distance with at the same time a large depth of field for recording an image scene. The small object distance leads to little installation space being required. This results in advantages for the integration into machines and plants, which can now be upgraded or be newly built. By way of example, the image sensor array according to the present invention can be retrofitted into machines where conventional IIP systems do not fit into the installation space thereof. Using the image sensor array also makes it possible to reduce machine size, which is accompanied by direct competitive advantages if a machine is newly built.

According to the present invention, the multiplicity of identical sensor elements spatially and functionally form a unit that belongs together; this unit can capture a contiguous image scene. To this end, the sensor cells are arranged in at least one row. In this constellation, the image sensor array forms a one-dimensional sensor cluster, which, in industrial surroundings, is particularly suitable for capturing tape. Here, adjacent sensor cells are electrically interconnected via the data interface. In a row, the end-side sensor cells then have one direct neighbor and hence at least one data interface whereas the remaining sensor cells respectively have two neighbors, which are electrically contacted to one another via respectively one data interface.

Here it is of particular importance that adjacent sensor cells have a common image capture region such that both capture the same sub-region of the image scene. As a result of the different perspectives, an image sensor from one of the two sensor cells can capture scene details that are not visible from the perspective of the image sensor in the other sensor cell. To this end, the evaluation unit of each sensor cell uses the image information in respect of the common capture region from the frame buffer of the adjacent sensor cell in order to determine the correlation of the image data such that it is possible to create a stereoscopic image of the capture region that is captured together by two adjacent sensor cells.

In an embodiment of the present invention, each sensor cell can, for example, have four data interfaces. As a result of this, it is possible to connect four sensor cells as neighbors to one sensor cell, and so a two-dimensional sensor array can be implemented. As a result, the sensor cells can be arranged in the form of a matrix such that the image sensor array forms a two-dimensional sensor cluster for capturing a two-dimensional image scene. By way of example, it is possible to form an image sensor array with a 3×3 matrix, comprising nine image sensors in three rows and three columns, or a 4×4 matrix, comprising sixteen sensor cells in four rows and four columns. With this, it is possible to, for example, construct square capture regions. It is also possible to construct capture regions that are not square as desired by selecting an n×m matrix-shaped array with n rows and m columns of sensor cells, where n does not equal m.

In terms of its geometry, a sensor cell can have a rectangular, more particularly square, design. As a result, it can be connected to respectively one more sensor cell, via the appropriate data interface, on all four side edges. This achieves a symmetric design of a sensor cell, and so this results in simple manufacture.

In an embodiment of the image sensor array of the present invention, the geometry of a sensor cell can, for example, be triangular. In this embodiment, a sensor cell can, for example, have three data interfaces, and so respectively one adjacent sensor cell can be connected to the three side edges.

In an embodiment of the present invention, the evaluation unit of a sensor cell can, for example, have video processors, the number of which at least corresponds to the number of direct neighbors of the sensor cell, with each video processor being associated with a directly adjacent sensor cell. Here, each video processor autonomously processes the image data from the overlapping capture region of the sensor cell to the adjacent sensor cell and, in the process, uses the image data of the latter. Accordingly, a sensor cell with four direct neighbors has four video processors, each of which independently evaluates the correlation of the image data.

In an embodiment of the present invention, the image sensors can, for example, be embodied as complementary metal oxide semiconductor (CMOS) sensors. They are also referred to as active pixel sensors (APS) and are advantageous in that each pixel can be processed separately by converting charges into voltages. Hence, a CMOS sensor can be flexibly read out by directly addressing the individual pixels. In doing so, multiple readouts and simultaneous readout of a number of pixels are also possible. As a result, the image data from specific regions of the capture region of an image sensor can be called individually and in a targeted manner. Such regions are also referred to as "regions of interest" (ROI). Thus, in an image sensor, the image data of that region of its capture region that overlaps with a region of the capture region of an adjacent sensor cell can be read out in a targeted manner.

In an embodiment of the image sensor array according to the present invention, all sensor cells can, for example, be formed on a common, more particularly plate-shaped, support element. An advantage of this is that a compact assembly for an IIP system is created which can be assembled in a quick and simple manner. Compared to this, the integration of conventional multi-camera IIP systems is characterized by protracted work for assembling and adjusting the systems. By contrast, an image sensor array according to the present invention can be preassembled at the factory and can be integrated into a production plant already adjusted such that down-times of the plant are reduced.

The common arrangement of all sensor cells on one support element provides the option of interconnecting a plurality of image capture apparatuses in a module-like manner, i.e., connecting them in a mechanical and functional manner. By way of example, the support element can be a printed-circuit board. Here, an array of 3×3 or 4×4 sensor cells can, for example, be assembled on the printed-circuit board. For reasons of space, it is advantageous to assemble the frame buffers and/or the evaluation units on the rear side of the support element. As a result, the image sensors, objective holders and the sensor optical systems can be assembled on the front side, i.e., on the side facing the image scene to be captured. As a result of the common assembly of all components on a support element, more particularly a printed-circuit board, the signal lines are kept to a minimum such that a high data transmission rate can be achieved. This is a precondition for real-time transmission of image data.

In an embodiment of the present invention, the evaluation units can, for example, be formed by programmable or, in the specific application, programmed logic modules. By way of example, so-called field programmable gate arrays (FPGAs) or application-specific integrated circuits (ASICs) can be used in this case. An advantage of these is that they can process the image data particularly quickly so that real-time processing of the image data can be achieved.

In order to transmit the image data and/or other control data between the adjacent sensor cells, the evaluation units can be interconnected in series over the data interfaces. The evaluation units can, for example, be interconnected via one or more bit-serial data channels so that a high data transmission rate is ensured.

As already mentioned above, the image sensor array according to the present invention can be connected in modular fashion to one or more further image sensor arrays of the aforementioned type in order to make a large image sensor array. As a result, it is possible to scale the overall capture region of the image sensor array. Hence, the image sensor array can be individually matched to the size of an image scene to be captured. By way of example, this can be used to construct planar, but also spherical or even cylindrical, sensor clusters. Thus, for example, a spherical, concave image sensor array is suitable for use in medicine, more particularly surgery, for example, for monitoring an operative intervention. A sensor array formed like a cluster can thus capture a large measurement region at a high resolution without a mechanical displacement unit being required. As a result, this is advantageous to the user due to lower maintenance, fewer wearing parts and a higher measurement rate. The scene resolution and, at the same time, the system computational power can be scaled.

In the case of conventional multi-camera IIP systems, replacing a failed camera is very complicated and can only be carried out by expert staff due to the present complicated adjustment or calibration. In the case of an arrangement according to the present invention of a plurality of individual image sensor arrays, such an individual array, a so-called cluster, can be replaced and the repair and calibration can be carried out at the factory. If a sensor fails as a result of a defect, adjacent sensors can assume the objects (with a reduced resolution).

In order to form a large-area image sensor array, the support element can be connected to at least one support element of a further image sensor array in an interlocking manner. The data connection between a first image sensor unit and a further image sensor arrays can, for example, be established via the data interfaces of the peripheral sensor cells, which do not have a closest neighbor in the unconnected state of an image sensor array. In doing so, these, but also the remaining data interfaces, can be respectively formed by a plug-in contact, a solder contact or a soldering jumper. In addition to the electrical contact between two sensor cells, a plug-in contact additionally achieves a mechanical connection therebetween, which can quickly and easily be removed again if required. In the case of a solder contact, a permanent connection can be established between the sensor cells by means of a ribbon cable. Solder contacts are advantageous in that there is no corrosion and hence ohmic contact resistance at the contact regions, which reduce the transmission quality.

One of the sensor cells can, for example, have a controller, by means of which the evaluation units can be connected to an external computer. Hence the controller forms the interface to a central computer unit and can, for example, be integrated into the series connection of the evaluation units. A single data interface to the outside ensures a cost-effective adaptation of the image sensor array to the control systems of the user.

Further features and advantages of the present invention will be explained in more detail on the basis of the following description of exemplary embodiments and the attached drawings.

FIG. 1 shows an arrangement of an elementary industrial image-processing system according to the prior art. Here, a camera 100 is connected to a PC 140. The camera 100 has a field of view 110, also referred to as capture region below, within which an object to be inspected 120, more particularly a component, is arranged, the surface of which forming the object plane 130 to be recorded. The camera records an image scene, in which the component 120 is inspected in respect of completeness and/or dimensional accuracy.

Figure 2:
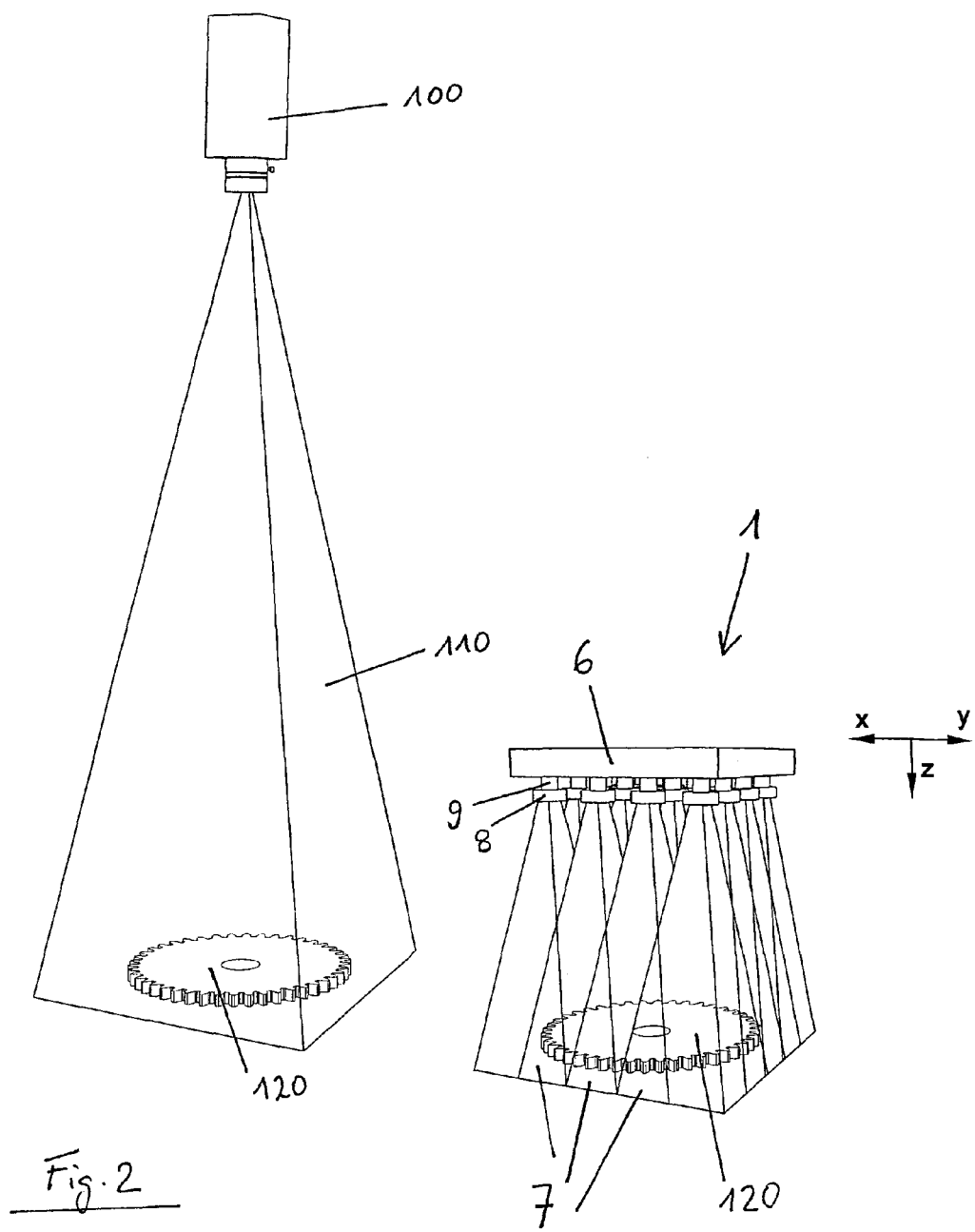
FIG. 2 shows a comparison between a conventional camera and the image sensor array according to the present invention.

FIG. 2 illustrates the comparison between a conventional camera 100 and an image sensor array 1 according to the present invention as a two-dimensional sensor cluster for visually recording an object 120. The overlapping fields of view 7 of adjacent image sensors 3, to which respectively one sensor optical system 8 with objective holder 9 is assigned and which are arranged together on a support element 6, result in additional scene information in a 2D sensor cluster 1, which information cannot be obtained by a conventional camera 100. The image sensor array is compatible to conventional cameras 100 in terms of signals, and so use can optionally be made of hardware and software from an IIP signal-processing chain. An interface is provided for this object, which interface couples the image sensor array to a typical IIP interface, e.g., to CameraLink, and is referred to as a cluster controller below.

Figure 3:
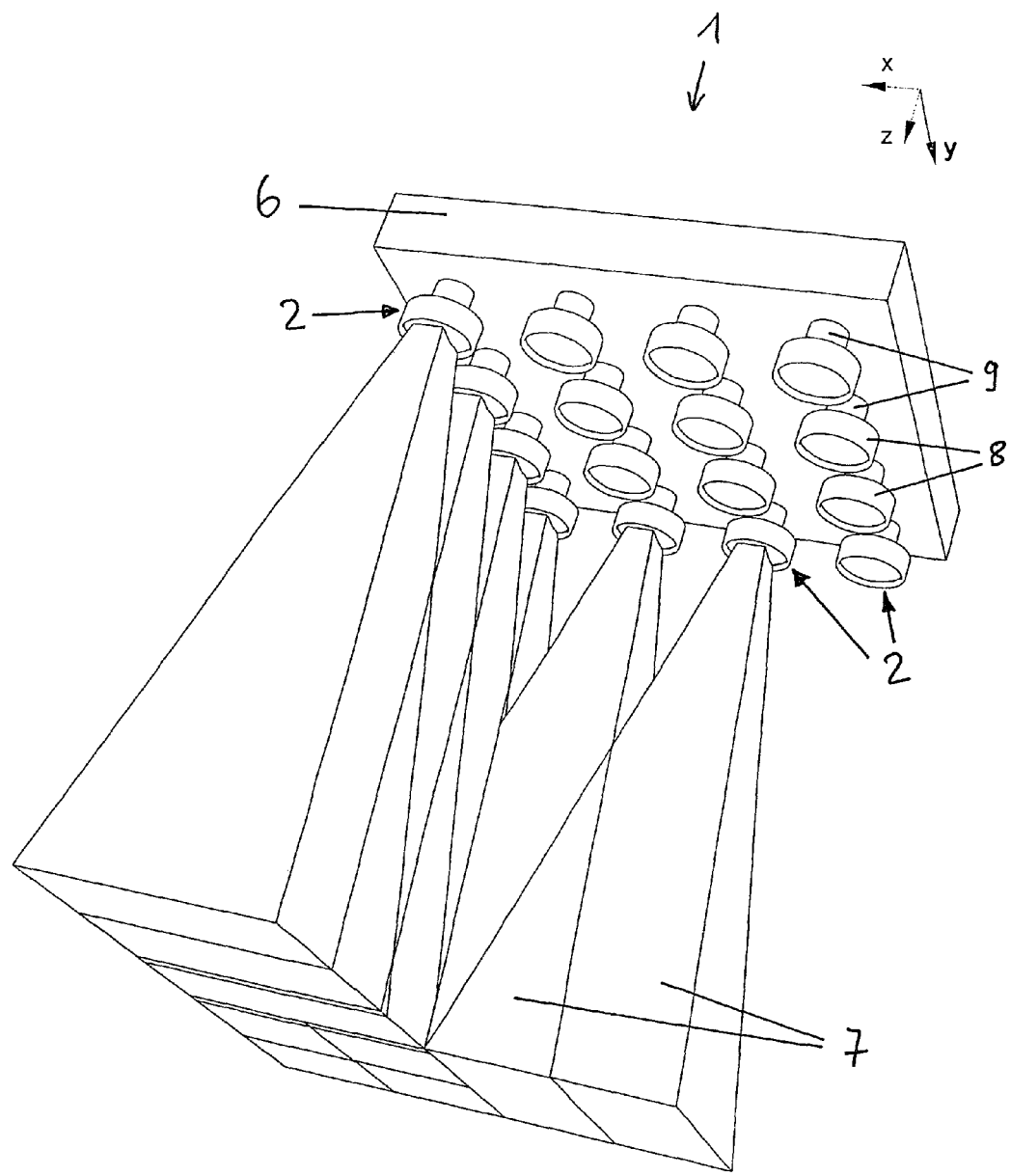
FIG. 3 shows a two-dimensional image sensor array in a perspective view with superimposed image capture regions of the image sensors.

FIG. 3 shows a perspective view of an image sensor array 1 according to the present invention with indicated fields of view 7, which overlap at adjacent sensor cells 2. The image sensor array forms an IIP component which, in a two-dimensional field, combines image sensors 3 and the corresponding lens packages, consisting of sensor optical system 8 and objective holder 9, as a compact module and allows a novel component for constructing IIP systems. Here, a sensor optical system 8, which is assembled on an objective holder 9, is assigned to each image sensor 3. The objective holders 9 of all sensor cells 2 are assembled on a support element 6 together with the image sensors 3 (not illustrated). The image sensor array 1 forms a module that can be connected to further modules. Here 4×4, i.e. sixteen, image sensors 3 are integrated into this module and equipped with evaluation units 4 in the form of digital logic units, and so modules can be joined as desired and without gaps, and, as a result of this, sensor clusters of arbitrary dimensions can be constructed. However, the smallest system dimension for solving an image-processing object comprises an image sensor array 1 as illustrated in FIG. 3. The greater the number of utilized modules is, the greater the measurement region is. Moreover, the resolution depends on the packing density of the sensor cells 2. The fields of view 7 of the image sensors 3 are superposed in the object plane as per FIG. 3. Each pixel in the scene to is captured by at least four image sensors 3, as a result of which algorithms for data fusion can be applied and stereoscopic methods for 3D image analysis can be used. In order to monitor the completeness of objects to be inspected, e.g., a weld seam or a solder point, a 2D sensor cluster as per FIG. 3 can, for example, establish a defect that cannot be imaged by a single conventional camera 100.

Figure 4A:
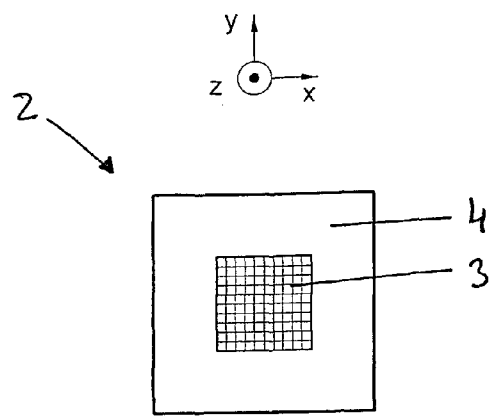
FIG. 4a shows a visual sensor cell of the image sensor array.

FIG. 4a shows a schematic illustration of a visual sensor cell 2. It comprises an image sensor 3 using CMOS technology, which has a plurality of pixels that can be read out. In the case of grayscale quantization of 10 bit per pixel, the commercially available CMOS image sensor 3 supplies a data stream of approximately 250 MBit/s. The CMOS image sensor 3 is distinguished by a large temperature range. Furthermore, the sensor cell has an evaluation unit 4, which is implemented in hardware logic in an FPGA. Furthermore, it comprises a frame buffer (not illustrated). The evaluation unit 4 in turn comprises five video processors as programmable logic modules, in which a plurality of processes, such as object finding, object measuring, etc., respectively run in parallel at the same time. That is to say a plurality of algorithms are applied in parallel and in real time to the video stream from an image sensor 3.

Figure 4B:
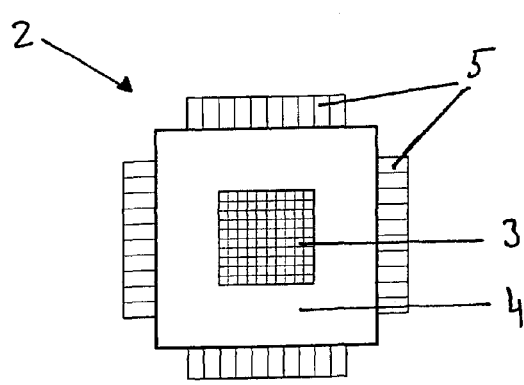
FIG. 4b shows a visual sensor cell of the image sensor array with data interfaces.

In FIG. 4b, the sensor cell 2 is imaged with four data interfaces 5, which can also be referred to as "data links". These can spatially define four edges of the sensor cell to which four additional sensor cells 2 can be attached. Here, there is an electrical connection between adjacent sensor cells 2 via the data interfaces 5. Each data interface 5 is used to interconnect the evaluation units 4 of directly adjacent sensor cells 2 by means of a plurality of bit-serial data channels. The data interfaces 5 realize the shortest possible transmission path for data interchange between two sensor cells 2. They form the technical basis of the multi-sensor architecture.

Figure 5:
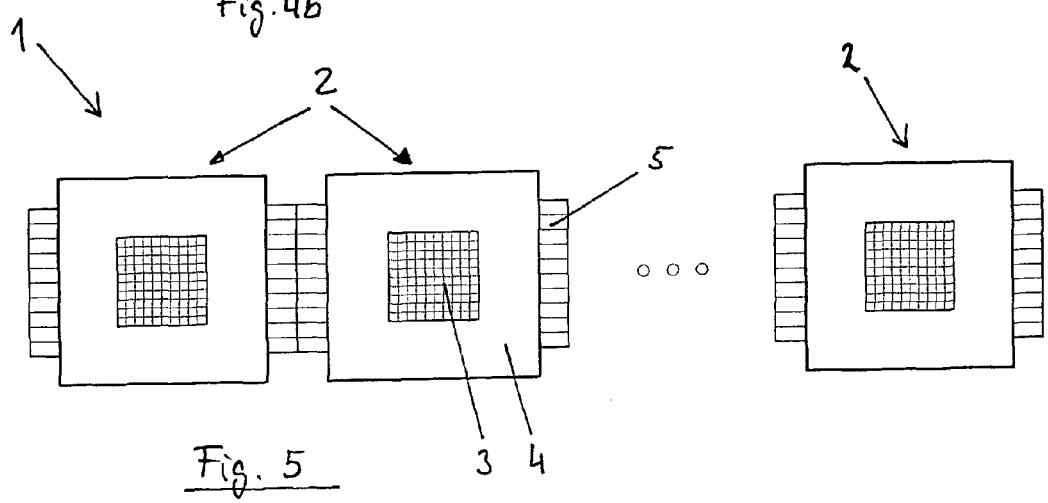
FIG. 5 shows a one-dimensional image sensor array as a chain of sensor cells.

FIG. 5 shows an image sensor array 1 with a multiplicity of sensor cells 2, which are only connected in a row. Here, only the first two and the last sensor cell 2 of the row are imaged. By way of example, 5, 10, 20 or else 80, 100 or more of such sensor cells 2 can be interconnected in this manner and form the image sensor array. It therefore constitutes a one-dimensional sensor cluster. Each frame buffer of a sensor cell 2 can be evaluated at the same time by every sensor cell 2 that is adjacent at the cell edges. By way of example, a row of 80 sensor cells 2 produces image data with an overall data rate of 20 Gigabit per second, which are preprocessed in the video processors. Such a 1D sensor cluster with 80 sensor cells has a length of 1600 mm and is suitable, for example, for inspecting tape-shaped materials. Here, the huge data amount from 80 image sensors, each with 250 MBit/s and 80 video processors, is, in real time, processed and linked, or evaluated in terms of its image by determining the correlation of the image data from the overlapping capture regions 7 of adjacent sensor cells. The image data is evaluated by the video processors implemented by hardware logic by applying a programmed correlation function, by means of which the correlation of the image data is determined. Here, the correlation is a measure specifying how closely pixels are related to one another. Position information associated with the measured object 120 or a detail of an object is derived on the basis of the correlation. This position information in turn can be used to make a statement in respect of the geometry, i.e., the length, width and height, of the measured object. By comparing these established geometry values to predetermined values, it is possible to assess deviations and hence the quality of the object.

Hence, the image data from adjacent sensor cells 2 are combined using methods from multi-sensorial data fusion. Compared to processing individual image scenes, the fused image information are used to draw further conclusions in respect of physical events, activities or situations. Methods from data fusion are complex and a mixture of mathematical and heuristic techniques from the fields of statistics, artificial intelligence, digital signal processing and decision theory. In the 1D sensor cluster, the data fusion is implemented by virtue of the fact that four image sensors are evaluated for each measurement point and, as a result of this, more robust measurement values are produced. The evaluation occurs directly downstream of the image sensors 3 in the data stream to the video processor.

Figure 6:
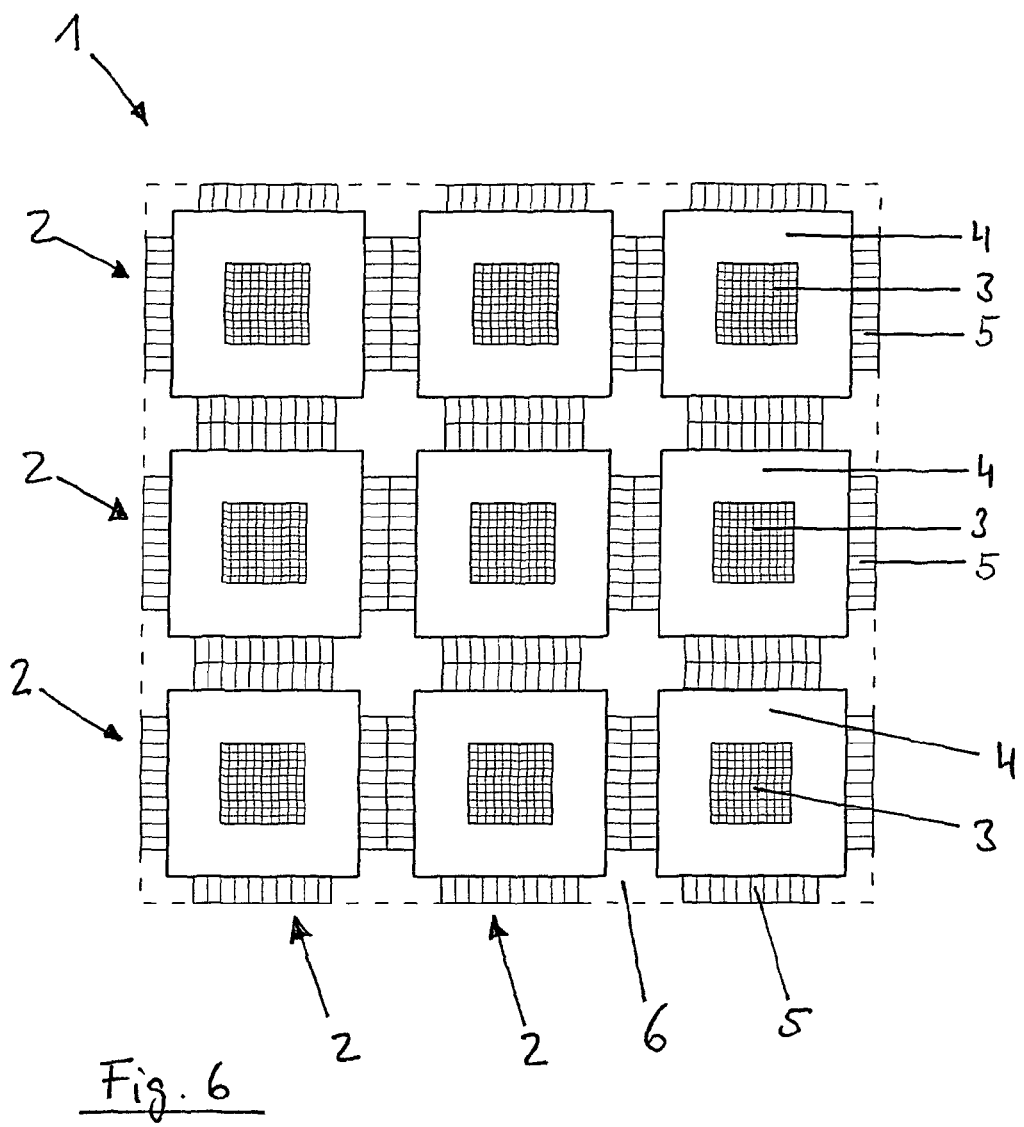
FIG. 6 shows a two-dimensional image sensor array with a matrix-like array of 3×3 sensor cells.

FIG. 6 shows a matrix-shaped arrangement of nine sensor cells 2 in an image sensor array 1, with three rows and three columns. Here there are nine image sensors 3, nine miniaturized objectives and nine evaluation units 4, and also twelve external data interfaces 5 to adjacent modules. The image sensors 3 of the sensor cells 2 are arranged equidistantly on a support plate 6. All sensor cells 2 have an identical design. Directly adjacent sensor cells are interconnected by one data interface in each case, and so the evaluation units 4 of the sensor cells can access the frame buffers of the respective adjacent sensor cells 2.

An evaluation logic unit 4 is assigned to each image sensor 3 and it has precisely one physical frame buffer. Each evaluation logic unit 4 of a sensor 3 can moreover access the frame buffer of the neighbor. In doing so, an evaluation logic unit 4 always only accesses part of the adjacent frame buffer, the so-called "region of interest" (ROI). The evaluation logic unit (4) of each image sensor 3 consists of a central video processor and four ROI video processors, which respectively process the ROI from the dedicated image sensor 3 and from the relevant neighbor in an autonomous manner. These processes occur simultaneously, i.e., in parallel.

Figure 7:
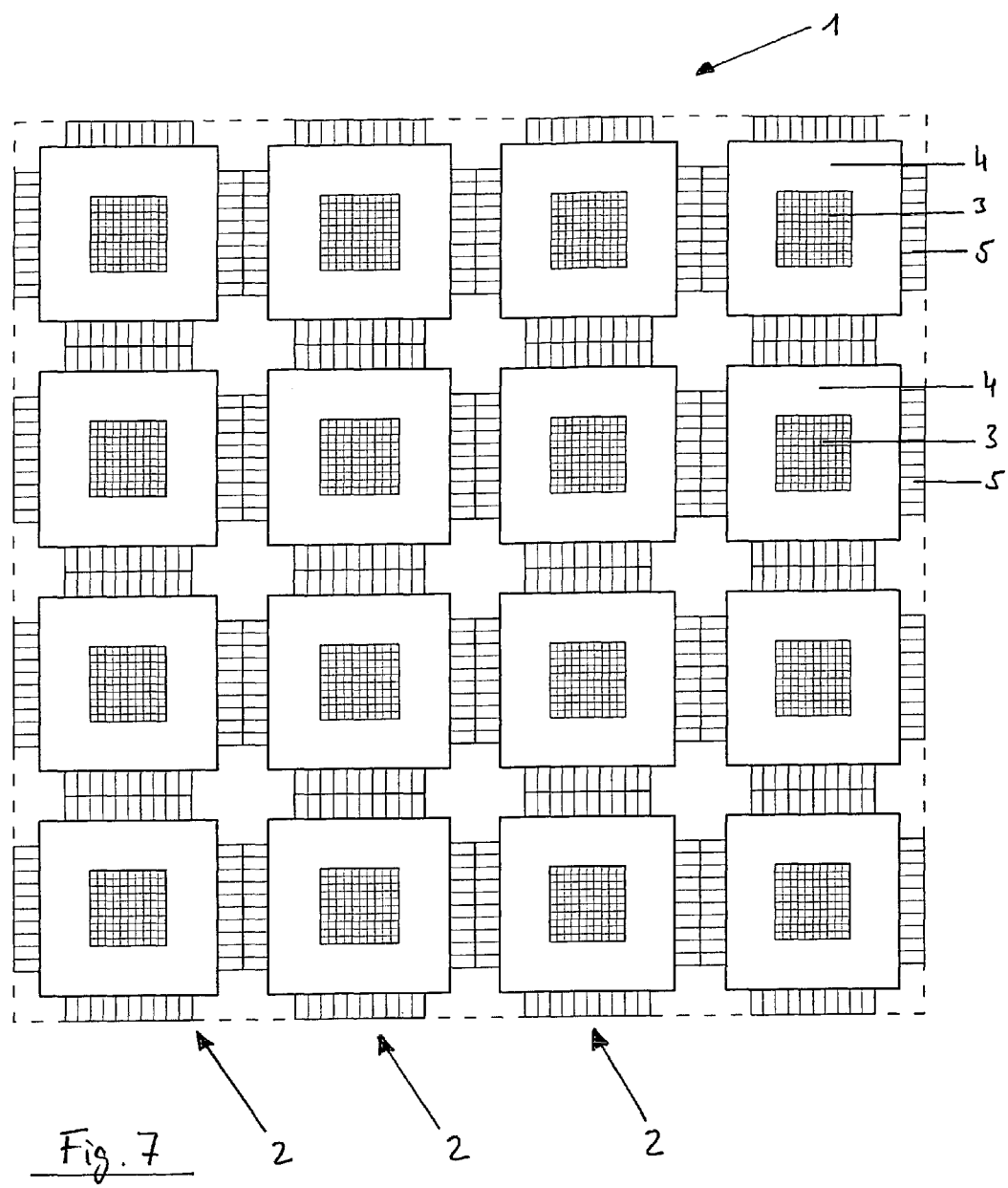
FIG. 7 shows a two-dimensional image sensor array with a matrix-like array of 4×4 sensor cells.

FIG. 7 shows a matrix-shaped arrangement of sixteen sensor cells 2 in an image sensor array 1, with four rows and four columns. Here there are sixteen image sensors 3, sixteen miniaturized objectives and sixteen evaluation units 4, and also sixteen external data interfaces 5 to adjacent modules. Otherwise, the arrangement corresponds to the one as per FIG. 6. The installation size of the support plate 6 is 80×80×20 mm$^3$.

Figure 8:
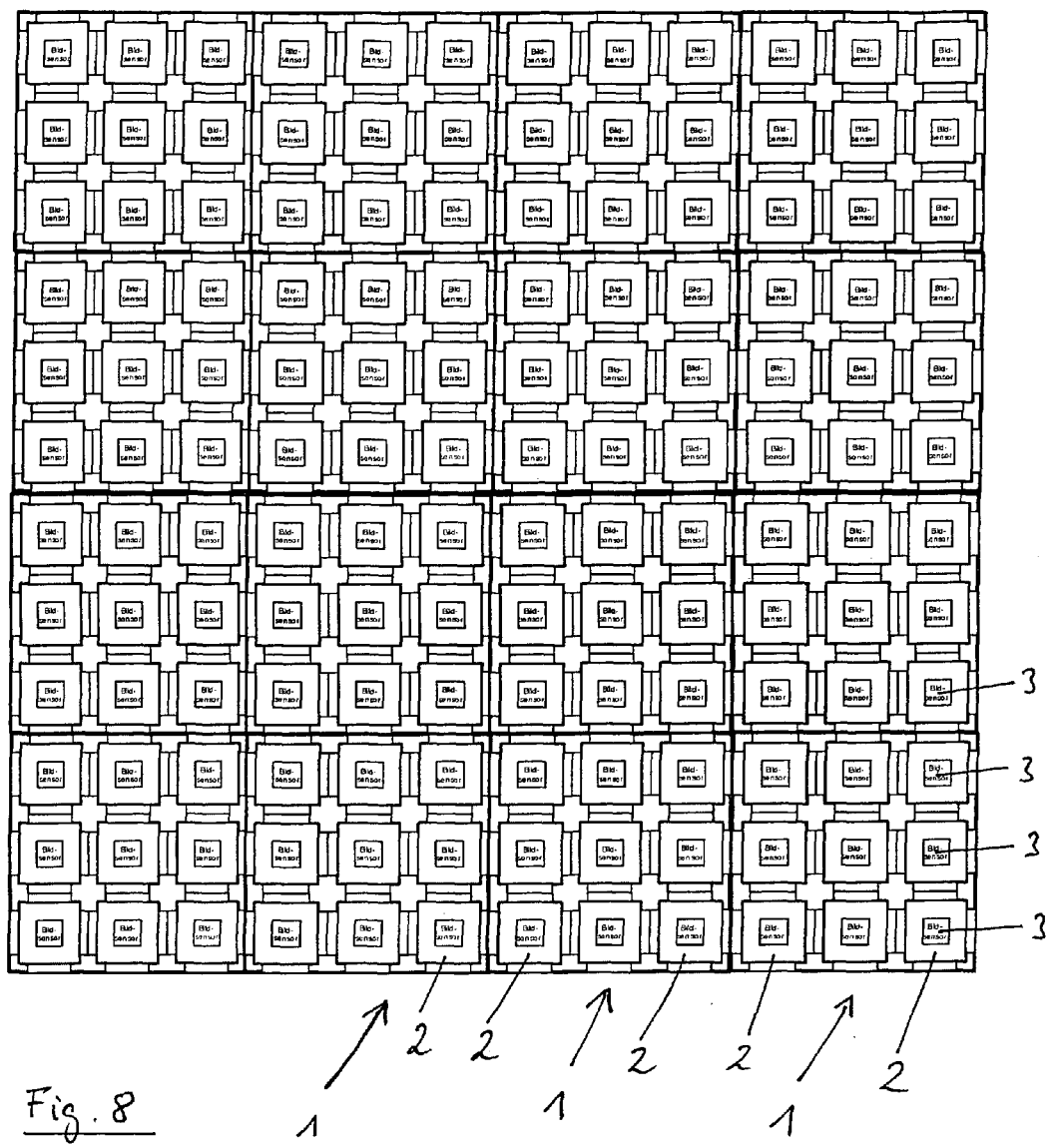
FIG. 8 shows a sensor cluster with 4×4 image sensor arrays made of 3×3 sensor cells.
Figure 10:
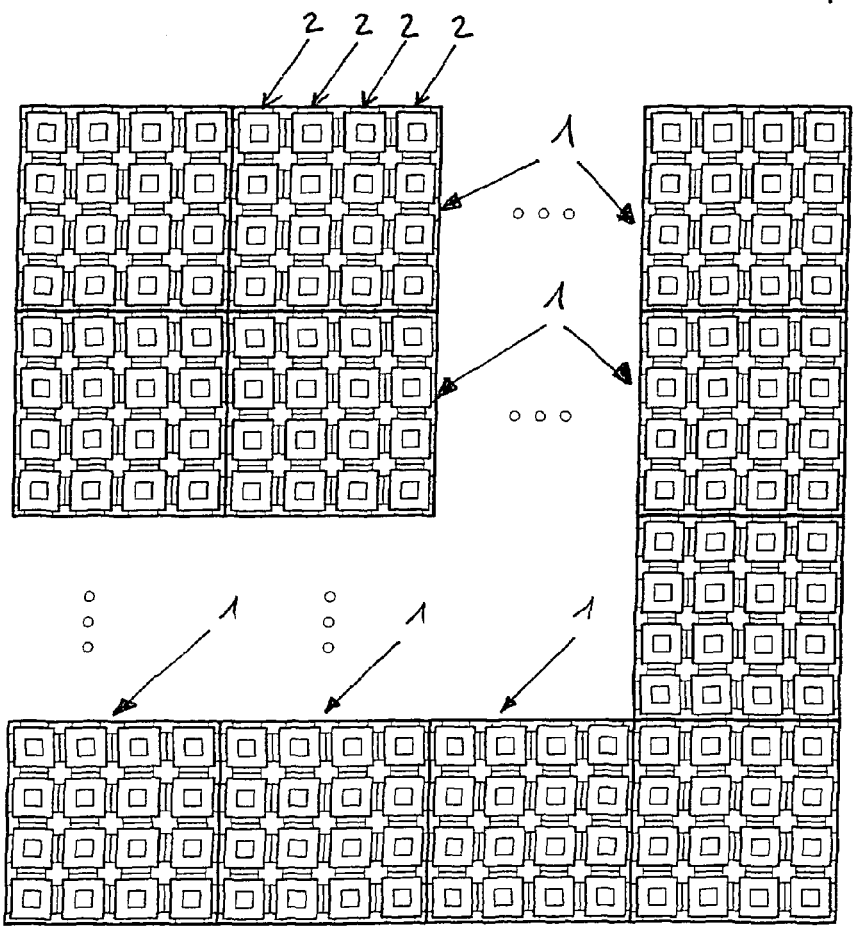
FIG. 10 shows a schematic illustration of the module-type connection of a plurality of image sensor arrays to form a two-dimensional sensor cluster.

FIG. 8 shows a two-dimensional sensor cluster made of 4×4 image sensor arrays 1 as per FIG. 6, which respectively have 3×3 sensor cells. In this manner, 144 image sensors 3 are combined to form a sensor cluster with a large capture region. FIG. 10 illustrates the module-like arrangement of arbitrarily many image sensor arrays 1 per column and row in order to obtain an n×m sensor cluster with n rows and m columns. Here, a symmetric array with n=m or else an asymmetric array with n≠m can be constructed. The individual "tiles" in each case comprise 4×4 sensor cells 2.

The transition from one tile to the next has the same data channel structure (data link) as the interconnections between the sensor cells 2 on a tile. The respective video processors do not "notice" a physical tile transition and need not consider this. It is only at the edge of a sensor cluster, i.e., at the outer edges of the outer tiles of a sensor cluster constructed from a plurality of tiles, that the respective central video processor will determine that communication can only be established with three neighbors (on the outer tile edge) or two neighbors (on the outer tile corner) instead of with four neighbors. Accordingly, it is only the available overlapping ROIs that are evaluated.

Hence, this creates a restriction for the user in that an image scene may only be so large that the image scene does not project beyond the center of the outer image sensors of a cluster. This means that, during the dimensioning of a sensor cluster, the user must always combine so many tiles that the knife fish or the image scene is entirely encompassed. Otherwise there are information deficits at the edges, in particular in the corners, of a cluster, which lead to reduction in quality of the image information despite redundancy in the ROI.

Figure 9:
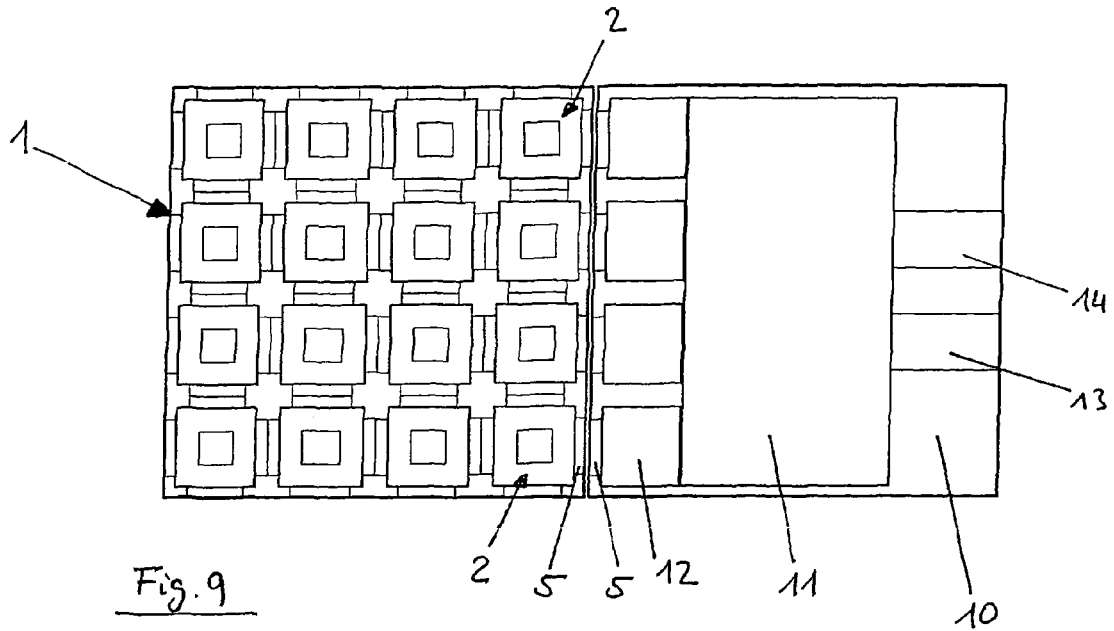
FIG. 9 shows an image sensor array with an interface card.

FIG. 9 illustrates the connection of an image sensor unit 1 to an interface card 10, which realizes an interface 11 to a processing PC. Here, provision is made for a TCP/IP connection 13 for connecting the image sensor array to a network and for a camera-link connection 14 for directly connecting the sensor array to the PC. The connection to the adjoining edge sensor cells 2 is established via data interfaces 5, as are also implemented between the sensor cells 2 of the image sensor array 1. Hardware logic units 12 control the data transmission to the interface 11.

Figure 11:
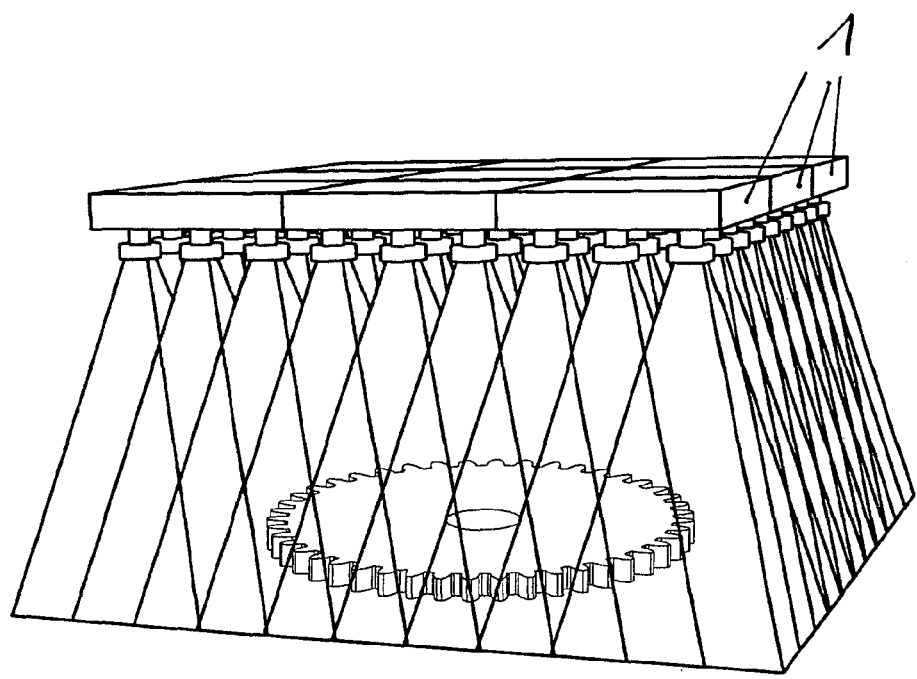
FIG. 11 shows a perspective view of a two-dimensional sensor cluster with nine image sensor arrays made of 3×3 sensor cells.

FIG. 11 shows a two-dimensional sensor cluster made of nine image sensor arrays, arranged in three rows and three columns in a matrix shape, with each image sensor array comprising nine sensor cells which are likewise arranged in three rows and three columns. A sensor cluster can consist of almost any number of image sensor arrays combined in a modular manner, which are also referred to as tiles or modules below. As per FIG. 11, each module contains a defined number of sensor cells 2, which respectively evaluate a section of the image scene. Each pixel in the scene is captured and evaluated by at least two adjacent sensor cells 2. The image sensors 3 are typically arranged in a rectangular matrix. In order to increase the packing density, the sensor elements 2 can also be arranged in a honeycomb shape.

In an embodiment of the present invention that has not been illustrated, it is possible for high-brightness light-emitting diodes (HB-LEDs) to be integrated between the sensors 3, the former ensuring a partial and directionally dependent illumination of the scene.

The image sensor array according to the present invention can be utilized universally in technical image processing. The sensor array is distinguished by a high scene resolution, small installation space, high imaging performance and high computational performance. As a result of these characteristics, it is possible to derive a multiplicity of new applications for solving technical problems and provide the user with economic advantages. Production plants that previously could not be equipped with industrial image processing can now be equipped and retrofitted.

The image sensor array 1 according to the present invention also harbors the potential of capturing the 3D world of industrial scenes. Adjacent image sensors 3 can observe object details from different perspectives and hence also obtain information in respect of the z-axis in addition to the xy-geometry.

The present invention is not limited to embodiments described herein; reference should be had to the appended claims.

What is claimed is:

1. An image sensor array for capturing image information for automatic image data processing, the image sensor array comprising a multiplicity of identical sensor cells, each sensor cell respectively comprising:
   at least one image sensor with a dedicated sensor optical system;
   a frame buffer configured to store image information from the at least one image sensor;
   an evaluation unit configured to process the image information; and
   at least one data interface to a directly adjacent sensor cell, the at least one data interface being configured to achieve each of an electrical contact and a mechanical connection with the directly adjacent sensor cell,
   wherein,
   the sensor cells are arranged in at least one row so that a capture region of an image sensor of the directly adjacent sensor cell overlaps,
   the at least one data interface to the directly adjacent sensor cell is configured to access the image data of the capture region, and
   the respective evaluation unit of the sensor cells is configured to determine a correlation of items of the image data in the capture region.

2. The image sensor array as recited in claim 1, wherein each sensor cell has four data interfaces.

3. The image sensor array as recited in claim 1, wherein the evaluation unit has at least four video processors, each of the at least four video processors being configured to autonomously process the image data from the overlapping capture region to the directly adjacent sensor cell.

4. The image sensor array as recited in claim 1, wherein the multiplicity of identical sensor cells are arranged in a matrix-like manner.

5. The image sensor array as recited in claim 4, wherein sixteen sensor cells are arranged equidistantly in four rows and four columns.

6. The image sensor array as recited in claim 1, wherein each of the at least one image sensor is a CMOS sensor.

7. The image sensor array as recited in claim 1, wherein the sensor cells are formed on a common support element.

8. The image sensor array as recited in claim 7, wherein the common support element is plate-shaped.

9. The image sensor array as recited in claim 7, wherein the common support element is a printed-circuit board.

10. The image sensor array as recited in claim 7, wherein at least one of the frame buffers and the evaluation units are assembled on a rear side of the common support element.

11. The image sensor array as recited in claim 1, wherein each evaluation unit comprises at least one programmable logic module.

12. The image sensor array as recited in claim 1, wherein each evaluation unit is interconnected in series via the at least one data interface.

13. The image sensor array as recited in claim 1, wherein each evaluation unit is interconnected via at least one bit-serial data channel.

14. The image sensor array as recited in claim 7, wherein the image sensor array is connected to at least one other image sensor array in a modular fashion.

15. The image sensor array as recited in claim 14, wherein the at least one other image sensor array is the image sensor array as recited in claim 1.

16. The image sensor array as recited in claim 15, wherein the common support element is connected to at least one common support element of the at least one other image sensor array in an interlocking manner.

17. The image sensor array as recited in claim 14, further comprising a data connection between the image sensor array and the at least one other image sensor array, wherein the data connection is established via the data interface of sensor cells disposed on a periphery.

18. The image sensor array as recited in claim 1, wherein each data interface is formed by a plug-in contact, a solder contact or a soldering jumper.

19. The image sensor array as recited in claim 1, wherein one sensor cell includes a controller configured to connect the evaluation unit to an external computer.

20. The image sensor array as recited in claim 1, wherein the electrical contact and the mechanical connection is provided by at least one of a plug-in contact, a solder contact, a soldering jumper, and a ribbon cable.

21. A method for capturing image information for automatic image processing with the image sensor array as recited claim 1, the method comprising:
- capturing a sub-region of an object plane with each of the at least one image sensor of a sensor cell so as to obtain image data of a capture region;
- storing the image data in a frame buffer of the sensor cell so that a capture region of the at least one image sensor from the directly adjacent sensor cell overlaps;
- assessing the image data of the overlapping capture region from the directly adjacent sensor cell via the data interface; and
- determining a correlation of items of the image data via the evaluation unit of each respective sensor cell.

22. An image sensor array for capturing image information for automatic image data processing, the image sensor array comprising a multiplicity of identical cameras, each camera respectively comprising:
- an image sensor with a dedicated sensor optical system;
- a frame buffer configured to store image information from the at least one image sensor;
- a video processor configured to process the image information; and
- at least one data interface to a directly adjacent camera, the at least one data interface being configured to achieve each of an electrical contact and a mechanical connection with the directly adjacent camera, wherein, the cameras are arranged in at least one of a row and a matrix so that a capture region of a camera of the directly adjacent camera overlaps, the at least one data interface to the directly adjacent camera is configured to access the image data of the capture region, and the respective video processor of the cameras is configured to determine a correlation of items of the image data in the capture region via a data pre-processing at the point of data generation so that image data is evaluated, and extracted scene information is generated, in each camera in real time.

23. The image sensor array as recited in claim 22, wherein the electrical contact and the mechanical connection is provided by at least one of a plug-in contact, a solder contact, a soldering jumper, and a ribbon cable.

* * * * *